(12) United States Patent
Hussey et al.

(10) Patent No.: US 12,109,308 B2
(45) Date of Patent: Oct. 8, 2024

(54) AQUEOUS FORMULATION COMPRISING 1-(4-{[4-(DIMETHYLAMINO)PIPERIDIN-1-YL]CARBONYL}PHENYL)-3-[4-(4,6-DIMORPHOLIN-4-YL-1,3,5-TRIAZIN-2-YL)PHENYL]UREA

(71) Applicant: Pfizer Inc., New York, NY (US)

(72) Inventors: James Joseph Hussey, Sandwich (GB); Andrew Gilbert Bright, Winchester (GB)

(73) Assignee: PFIZER INC., New York, NY (US)

(*) Notice: Subject to any disclaimer, the term of this patent is extended or adjusted under 35 U.S.C. 154(b) by 578 days.

(21) Appl. No.: 15/734,147

(22) PCT Filed: Jun. 4, 2019

(86) PCT No.: PCT/IB2019/054643
§ 371 (c)(1),
(2) Date: Dec. 1, 2020

(87) PCT Pub. No.: WO2019/234632
PCT Pub. Date: Dec. 12, 2019

(65) Prior Publication Data
US 2021/0212944 A1 Jul. 15, 2021

Related U.S. Application Data

(60) Provisional application No. 62/681,722, filed on Jun. 7, 2018, provisional application No. 62/754,651, filed on Nov. 2, 2018, provisional application No. 62/796,133, filed on Jan. 24, 2019, provisional application No. 62/841,882, filed on May 2, 2019.

(51) Int. Cl.
| | |
|---|---|
| *A61K 9/08* | (2006.01) |
| *A61K 9/00* | (2006.01) |
| *A61K 9/19* | (2006.01) |
| *A61K 31/5377* | (2006.01) |
| *A61K 47/02* | (2006.01) |
| *A61K 47/12* | (2006.01) |
| *A61K 47/26* | (2006.01) |
| *A61K 47/40* | (2006.01) |
| *A61P 35/00* | (2006.01) |

(52) U.S. Cl.
CPC .............. *A61K 9/08* (2013.01); *A61K 9/0019* (2013.01); *A61K 9/19* (2013.01); *A61K 31/5377* (2013.01); *A61K 47/02* (2013.01); *A61K 47/12* (2013.01); *A61K 47/26* (2013.01); *A61K 47/40* (2013.01); *A61P 35/00* (2018.01)

(58) Field of Classification Search
None
See application file for complete search history.

(56) References Cited

U.S. PATENT DOCUMENTS

| | | | |
|---|---|---|---|
| 4,727,064 A * | 2/1988 | Pitha | .................. C08B 37/0012 106/205.01 |
| 4,983,586 A * | 1/1991 | Bodor | ................ A61K 47/6951 514/777 |
| 5,298,410 A * | 3/1994 | Phillips | .................. A61K 47/60 435/189 |
| 8,039,469 B2 | 10/2011 | Venkatesan et al. | |
| 8,217,036 B2 | 7/2012 | Venkatesan et al. | |
| 8,445,486 B2 | 5/2013 | Venkatesan et al. | |
| 8,575,159 B2 | 11/2013 | Venkatesan et al. | |
| 8,748,421 B2 | 6/2014 | Venkatesan et al. | |
| 8,859,542 B2 | 10/2014 | Venkatesan et al. | |
| 9,174,963 B2 | 11/2015 | Venkatesan et al. | |
| 9,895,378 B2 | 2/2018 | Bagrodia et al. | |
| 10,022,381 B2 | 7/2018 | Venkatesan et al. | |
| 10,071,100 B2 | 9/2018 | Bagrodia et al. | |
| 10,172,942 B2 | 1/2019 | Back et al. | |
| 10,660,959 B2 | 5/2020 | Back et al. | |
| 11,541,058 B2 | 1/2023 | Hussey et al. | |
| 2003/0068340 A1 | 4/2003 | Cappola et al. | |
| 2009/0291079 A1 | 11/2009 | Venkatesan et al. | |
| 2011/0312955 A1 | 12/2011 | Venkatesan et al. | |
| 2013/0005723 A1 | 1/2013 | Venkatesan et al. | |
| 2013/0109670 A1 | 5/2013 | Venkatesan et al. | |
| 2013/0315865 A1 | 11/2013 | Venkatesan et al. | |
| 2014/0248239 A1 | 9/2014 | Venkatesan et al. | |
| 2015/0011752 A1 | 1/2015 | Venkatesan et al. | |

(Continued)

FOREIGN PATENT DOCUMENTS

| | | |
|---|---|---|
| CN | 102036995 A | 4/2011 |
| CN | 106163503 A | 11/2016 |

(Continued)

OTHER PUBLICATIONS

International Preliminary Report on Patentability, PCT/IB2019/054643, dated Dec. 8, 2020, 7 pages.
International Search Report and Written Opinion, PCT/IB2019/054643, dated Oct. 7, 2019, 9 pages.
Venkatesan, A. et al., "Bis(morpholino-1,3,5-triazine) Derivatives: Potent Adenosine 50-Triphosphate Competitive Phosphatidylinositol-3-kinase/Mammalian Target of Rapamycin Inhibitors: Discovery of Compound 26 (PKI-587), a Highly Efficacious Dual Inhibitor," J. Med. Chem., vol. 53: 2636-2645 (2010).

(Continued)

*Primary Examiner* — Sin J Lee
(74) *Attorney, Agent, or Firm* — Nelson Mullins Riley & Scarborough LLP; Jane E. Remillard, Esq.; Jill Gorny Sloper, Esq.

(57) ABSTRACT

The present invention relates to a pharmaceutical aqueous formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, or a pharmaceutically acceptable organic or inorganic acid salt thereof, a pharmaceutically acceptable organic or inorganic acid, a pharmaceutically acceptable beta- or gamma-cyclodextrin and water, that is a clear solution, with the proviso that the organic or inorganic acid (including a salt thereof) is not a sulphonic acid. Such a formulation is particularly suitable for intravenous or parenteral administration to a patient.

28 Claims, 1 Drawing Sheet

(56) References Cited

U.S. PATENT DOCUMENTS

| | | |
|---|---|---|
| 2015/0258102 A1 | 9/2015 | Bagrodia et al. |
| 2017/0119778 A1 | 5/2017 | Venkatesan et al. |
| 2017/0360935 A1* | 12/2017 | Back .................. C07D 401/12 |
| 2018/0125854 A1 | 5/2018 | Bagrodia et al. |
| 2019/0105390 A1 | 4/2019 | Back et al. |
| 2021/0177857 A1 | 6/2021 | Bagrodia et al. |
| 2021/0267988 A1 | 9/2021 | Hussey et al. |
| 2023/0218628 A1 | 7/2023 | Hussey et al. |

FOREIGN PATENT DOCUMENTS

| | | |
|---|---|---|
| KR | 101829705 B1 | 2/2018 |
| WO | 2009/143313 A1 | 11/2009 |
| WO | 2015138835 A1 | 9/2015 |
| WO | 2016/097949 A1 | 6/2016 |
| WO | 2019/038657 A1 | 2/2019 |

OTHER PUBLICATIONS

Fedorova, P-Y., et al. "Natural cyclic oligosaccharides-cyclodextrins in drug delivery systems" Medical Bulletin of Bashkortostan, vol. 6(125): 1311-1234 (2011).

Redenti, E. et al., "Drug/cyclodextrin/hydroxy acid multicomponent systems. Properties and pharmaceutical applications"; Journal of Pharmaceutical Sciences, vol. 89, Issue 1:8 pages (2000).

U.S. Appl. No. 18/072,246, filed Nov. 30, 2022, Kristin Ann Vajda, US 20230218628.

Beni, S. et al., "Cyclodextrin/imatinib complexation: Binding mode and charge dependent stabilities," European J of Pharm Sci., vol. 30:167-174 (2007).

Demirel, M. et al., "Inclusion complexes of ketoconazole with beta-cyclodextrin:physicochemical characterization and in vitro dissolution behaviour of its vaginal suppositories," J Ind Phenom Macrocycl Chem., vol. 70:437-445 (2011).

Muankaew, C. et al., "Cyclodextrin-Based Formulations: A Non-Invasive Platform for Targeted Drug Delivery," Basic & clinical Pharmacology & Toxicology, vol. 122: 46-55 (2018).

Redenti, E. et al., "Drug/cyclodextrin/hydroxy acid multicomponent systems. Properties and pharmaceutical applications"; Journal of Pharmaceutical Sciences, vol. 89, Issue 1:8 pages (1999).

Uekama, K. et al., "Enhanced bioavailability of digoxin by gamma-cyclodextrin complexation," J Pharmacobiodyn., vol. 4(9):735-737 (1981).

* cited by examiner

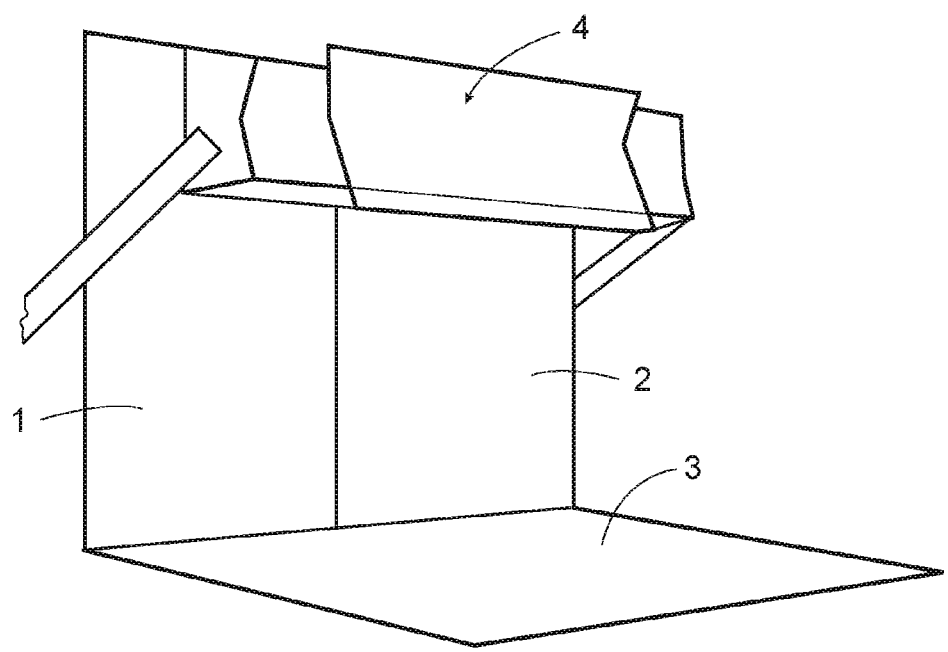

AQUEOUS FORMULATION COMPRISING 1-(4-{[4-(DIMETHYLAMINO)PIPERIDIN-1-YL]CARBONYL}PHENYL)-3-[4-(4,6-DIMORPHOLIN-4-YL-1,3,5-TRIAZIN-2-YL)PHENYL]UREA

CROSS-REFERENCE TO RELATED APPLICATIONS

This Application is the national stage filing under 35 U.S.C. 371 of Patent Cooperation Treaty Patent Application No. PCT/IB2019/054643, filed Jun. 4, 2019, which claims the benefit of priority from United States Provisional Application Nos. 62/841,882 filed May 2, 2019, 62/796,133, filed Jan. 24, 2019, 62/754,651, filed Nov. 2, 2018, and 62/681,722 filed Jun. 7, 2018, the contents of each of which are hereby incorporated by reference in their entirety.

FORMULATION

The present invention relates to a pharmaceutical formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, or a pharmaceutically acceptable organic or inorganic acid salt thereof. More specifically, the present invention relates to a pharmaceutical aqueous formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, or a pharmaceutically acceptable organic or inorganic acid salt thereof, that is a clear solution. Such a formulation is particularly suitable for intravenous or parenteral administration to a patient.

BACKGROUND 1-(4-{[4-(Dimethylamino)piperidin-1-yl]carbonyl}phenyl)-3-[4-(4,6-dimorpholin-4-yl-1,3,5-triazin-2-yl)phenyl]urea, and preparations thereof, are disclosed in WO2009/143313. The compound is an inhibitor of PI3 kinase and mTOR that is useful for the treatment of cancer.

A crystalline form of 1-(4-{[4-(dimethylamino)piperidin-1-yl]carbonyl}phenyl)-3-[4-(4,6-dimorpholin-4-yl-1,3,5-triazin-2-yl)phenyl]urea, and process for the preparation thereof, are disclosed in WO2010/096619.

WO2016/097949 describes a pharmaceutical aqueous solution formulation suitable for intravenous administration comprising (i) 1-(4-{[4-(dimethylamino)piperidin-1-yl]carbonyl}phenyl)-3-[4-(4,6-dimorpholin-4-yl-1,3,5-triazin-2-yl)phenyl]urea, or a lactate salt thereof, lactic acid and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of less than 6 mg/ml and sufficient lactic acid is present to provide a clear solution; or (ii) 1-(4-{[4-(dimethylamino)piperidin-1-yl]carbonyl}phenyl)-3-[4-(4,6-dimorpholin-4-yl-1,3,5-triazin-2-yl)phenyl]urea, or a phosphate salt thereof, orthophosphoric acid and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of less than 4 mg/ml and sufficient orthophosphoric acid is present to provide a clear solution. Lyophilisation of such formulations are also described. Of the many acids tested (i.e. citric acid, succinic acid, acetic acid, glycine, tartaric acid, maleic acid, malic acid, hydrochloric acid, lactic acid and orthophosphoric acid), only lactic acid and orthophosphoric acid are found to be capable of achieving a clear solution with a concentration of 1-(4-{[4-(dimethylamino)piperidin-1-yl]carbonyl}phenyl)-3-[4-(4,6-dimorpholin-4-yl-1,3,5-triazin-2-yl)phenyl]urea of 3 mg/ml or above.

1-(4-{[4-(Dimethylamino)piperidin-1-yl]carbonyl}phenyl)-3-[4-(4,6-dimorpholin-4-yl-1,3,5-triazin-2-yl)phenyl]urea, also known as gedatolisib, has the chemical structure:

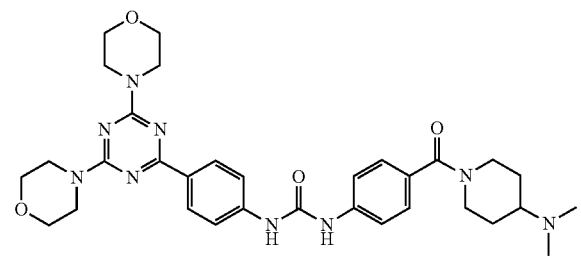

1-(4-{[4-(dimethylamino)piperidin-1-yl]carbonyl}phenyl)-3-[4-(4,6-dimorpholin-4-yl-1,3,5-triazin-2-yl)phenyl]urea 1-(4-{[4-(Dimethylamino)piperidin-1-yl]carbonyl}phenyl)-3-[4-(4,6-dimorpholin-4-yl-1,3,5-triazin-2-yl)phenyl]urea may be prepared in crystalline form and is chemically and physically stable at 25° C. and 60% Relative Humidity (RH) for up to 3 years in this form. However, this free base is insufficiently water soluble to allow the preparation of an aqueous solution formulation suitable for intravenous or parenteral administration at the therapeutic dosage levels required.

There is a need to develop a pharmaceutically acceptable aqueous solution formulation of 1-(4-{[4-(dimethylamino)piperidin-1-yl]carbonyl}phenyl)-3-[4-(4,6-dimorpholin-4-yl-1,3,5-triazin-2-yl)phenyl]urea that preferably is (a) chemically stable on storage (e.g. at 25° C. and 60% RH), (b) that will facilitate effective intravenous (or parenteral) administration of the drug to a mammal, including a human being, and (c), preferably, to achieve a solution concentration of 1-(4-{[4-(dimethylamino)piperidin-1-yl]carbonyl}phenyl)-3-[4-(4,6-dimorpholin-4-yl-1,3,5-triazin-2-yl)phenyl]urea that is at least 6 mg/ml.

SUMMARY

A solution concentration of 1-(4-{[4-(dimethylamino)piperidin-1-yl]carbonyl}phenyl)-3-[4-(4,6-dimorpholin-4-yl-1,3,5-triazin-2-yl)phenyl]urea that is at least 6 mg/ml is desirable to allow dose administration to subjects using a single vial presentation of the commercial drug product. A lyophilised drug product (for reconstitution) containing less than 6 mg/ml drug product solution will require multiple vials to deliver the required therapeutic dose. A multiple vial approach to dose delivery is not desirable given current regulatory expectations for these product types.

Preferably, the formulation is suitable for intravenous or parenteral administration of 1-(4-{[4-(dimethylamino)piperidin-1-yl]carbonyl}phenyl)-3-[4-(4,6-dimorpholin-4-yl-1,3,5-triazin-2-yl)phenyl]urea in view of the particular pharmacokinetic and bioavailability characteristics of this drug.

It is essential that an intravenous formulation of any drug is a solution to facilitate safe and effective administration to a patient. It must be particle-free, and not form a gel or suspension. A clear, aqueous solution is preferred.

A "clear solution" is defined herein as a visually clear solution, which may bear a solution opalescence, that is essentially free from any visible particulates that can be observed on a visual inspection. Generally, if any particulate matter is observed, the formulation is not suitable for intravenous administration and should not be utilised as occlusion of blood vessels may occur. Accordingly, in view of the qualitative nature of the visual test, the term "essentially free from any visible particulates" is usually applied when no visible particulate matter is observed.

Particulate matter may be defined as follows:

speck—discrete particle whose shape cannot be determined without magnification smoke or swirl—fine particles that look like smoke or a tornado and usually originate from the sample vial floor and twist upward as the vial is swirled flocculent material—loosely aggregated particles or soft flakes particulates with a definite shape or characteristic can be described as glass-like, metallic-looking, etc.

The visual inspection can be conducted in accordance with the method defined in European Pharmacopoeia Method 2.9.20 entitled "Particulate contamination: visible particles" (see FIG. 1). This method determines particulate contamination of injections and infusions by extraneous, mobile, undissolved particles, other than gas bubbles, that may be present in the solutions. The test is intended to provide a simple procedure for the visual assessment of the quality of parenteral solutions as regards visible particles.

The Method states: "Remove any adherent labels from the container and wash and dry the outside. Gently swirl or invert the container, ensuring that air bubbles are not introduced, and observe for about 5 seconds in front of the white panel. Repeat the procedure in front of the black panel. Record the presence of any particles."

A suitable method in accordance with European Pharmacopoeia Method 2.9.20 that has been used for the present invention is described in Example 1(i).

Other validated methods may be also be used for the dermination of if any visible particulates are present. Such methods include Optical Polarised Microscopy ("OPM"). A suitable OPM method that has been used for the present invention is described in Example 1(ii).

Without being bound by theory, any opalescent hue may be caused by chromonic liquid crystal formation. Chromonic liquid crystals are formed by the formation of pi-pi stacked aromatic sections of a molecule forming column like stacks of dimers, trimers and low molecular weight oligomers of the molecules. The stacks that form can be shown via OPM to be non-crystalline microstructures associated to a chromonic liquid crystal. The non-crystalline microstructures exhibit interactions that are not permanent and there is movement to maintain the system in a free energy equilibrium. The opalescence of the solution comes from the alteration of the refractive index of the solution due to the formation of these stacks. OPM micrographs of the solutions will show that there is no crystalline material present and instead there is a chromonic liquid crystal phase. The presence of a liquid crystal phase results in a solution with opacity and/or opalescence due to a difference in refractive index within the solution formed. For a discussion on liquid crystal formation see "Optical Properties of Condensed Matter and Applications", Jai Singh (Editor), ISBN: 978-0-470-02193-4, Wiley, October 2006.

It has now been unexpectedly found that by use of a pharmaceutically acceptable beta- or gamma-cyclodextrin, pharmaceutical aqueous formulations can be prepared as a clear solution comprising (a) a solution concentration of 1-(4-{[4-(dimethylamino)piperidin-1-yl]carbonyl}phenyl)-3-[4-(4,6-dimorpholin-4-yl-1,3,5-triazin-2-yl)phenyl]urea that is significantly above 6 mg/ml and (b) one of a range of pharmaceutically acceptable organic or inorganic acids.

DESCRIPTION OF THE DRAWINGS

FIG. 1 reproduces FIG. 2.9.20.-1 of the publication "European Pharmacopoeia Method 2.9.20" and describes an apparatus consisting of a viewing station comprising: a matt black panel (1) of appropriate size held in a vertical position; a non-glare white panel (2) of appropriate size held in a vertical position next to the black panel; a non-glare white panel (3) of appropriate size held in a horizontal position at the base of the verticle panels; and an adjustable lampholder (4) fitted with a suitable, shaded, white-light source and with a suitable light diffuser (a viewing illuminator containing two 13 Watt fluorescent tubes, each 525 mm in length, is suitable). The intensity of illumination at the viewing point is maintained between 2000 lux and 3750 lux, although higher values are preferable for coloured glass and plastic containers.

DETAILED DESCRIPTION

Accordingly, the present invention relates to a pharmaceutical aqueous formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, or a pharmaceutically acceptable organic or inorganic acid salt thereof, a pharmaceutically acceptable organic or inorganic acid, a pharmaceutically acceptable beta- or gamma-cyclodextrin and water, that is a clear solution, with the proviso that the organic or inorganic acid (including a salt thereof) is not a sulphonic acid (hereafter "the formulation of the invention").

More specifically, the present invention relates to a pharmaceutical aqueous formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, or a pharmaceutically acceptable organic or inorganic acid salt thereof, a pharmaceutically acceptable organic or inorganic acid, a pharmaceutically acceptable beta- or gamma-cyclodextrin and water, wherein sufficient of the pharmaceutically acceptable organic or inorganic acid and pharmaceutically acceptable beta- or gamma-cyclodextrin are present to provide a clear solution, with the proviso that the organic or inorganic acid (including a salt thereof) is not a sulphonic acid.

In an embodiment of the invention is provided a pharmaceutical aqueous formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, a pharmaceutically acceptable organic or inorganic acid, a pharmaceutically acceptable beta- or gamma-cyclodextrin and water, wherein sufficient of the pharmaceutically acceptable organic or inorganic acid and pharmaceutically acceptable beta- or gamma-cyclodextrin are present to provide a clear solution, with the proviso that the organic or inorganic acid (including a salt thereof) is not a sulphonic acid.

In an embodiment of the invention is provided a pharmaceutical aqueous formulation comprising a pharmaceutically acceptable organic or inorganic acid salt of 1-(4-{[4-(dimethylamino)piperidin-1-yl]carbonyl}phenyl)-3-[4-(4,6-dimorpholin-4-yl-1,3,5-triazin-2-yl)phenyl]urea, a pharmaceutically acceptable organic or inorganic acid, a pharmaceutically acceptable beta- or gamma-cyclodextrin and water, wherein sufficient of the pharmaceutically acceptable organic or inorganic acid and pharmaceutically acceptable beta- or gamma-cyclodextrin are present to provide a clear solution, with the proviso that the organic or inorganic acid (including a salt thereof) is not a sulphonic acid.

In such embodiments, where applicable, the acid forming the pharmaceutically acceptable organic or inorganic acid salt, and the pharmaceutically acceptable organic or inorganic acid, preferably are the same.

Preferably, the pharmaceutically acceptable organic acid used (including for a salt thereof) is lactic acid, tartaric acid, malic acid, citric acid, succinic acid, acetic acid or maleic acid. The acid may be used in its racemic form, or as a single stereoisomeric form (or mixtures thereof), where applicable.

Preferably, the pharmaceutically acceptable inorganic acid used (including for a salt thereof) is hydrochloric acid or orthophosphoric acid.

Examples of a pharmaceutically acceptable beta-cyclodextrin are 2-hydroxypropyl-beta-cyclodextrin and sulphobutylether-β-cyclodextrin (SBECD). Examples of such a pharmaceutically acceptable gamma-cyclodextrin are gamma-cyclodextrin and 2-hydroxypropyl-gamma-cyclodextrin. Preferably, hydroxypropyl-beta-cyclodextrin is used in the formulations of the invention. By use of a pharmaceutically acceptable beta- or gamma-cyclodextrin it has been found that clear solutions may be achieved with no opalescence and/or containing higher concentrations of 1-(4-{[4-(dimethylamino)piperidin-1-yl]carbonyl}phenyl)-3-[4-(4,6-dimorpholin-4-yl-1,3,5-triazin-2-yl)phenyl]urea than are obtainable in the absence of the cyclodextrin component.

In an embodiment of the invention is provided a pharmaceutical aqueous formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, or a pharmaceutically acceptable organic or inorganic acid salt thereof, a pharmaceutically acceptable organic or inorganic acid, a pharmaceutically acceptable beta- or gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of at least 6 mg/ml and wherein sufficient of the pharmaceutically acceptable organic or inorganic acid and pharmaceutically acceptable beta- or gamma-cyclodextrin are present to provide a clear solution, with the proviso that the organic or inorganic acid (including a salt thereof) is not a sulphonic acid.

In an embodiment of the invention is provided a pharmaceutical aqueous formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, a pharmaceutically acceptable organic or inorganic acid, a pharmaceutically acceptable beta- or gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of at least 6 mg/ml and wherein sufficient of the pharmaceutically acceptable organic or inorganic acid and pharmaceutically acceptable beta- or gamma-cyclodextrin are present to provide a clear solution, with the proviso that the organic or inorganic acid (including a salt thereof) is not a sulphonic acid.

In an embodiment of the invention is provided a pharmaceutical aqueous formulation comprising a pharmaceutically acceptable organic or inorganic acid salt of 1-(4-{[4-(dimethylamino)piperidin-1-yl]carbonyl}phenyl)-3-[4-(4,6-dimorpholin-4-yl-1,3,5-triazin-2-yl)phenyl]urea, a pharmaceutically acceptable organic or inorganic acid, a pharmaceutically acceptable beta- or gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of at least 6 mg/ml and wherein sufficient of the pharmaceutically acceptable organic or inorganic acid and pharmaceutically acceptable beta- or gamma-cyclodextrin are present to provide a clear solution, with the proviso that the organic or inorganic acid (including a salt thereof) is not a sulphonic acid.

Lactic Acid Formulations

In an embodiment of the invention is provided a pharmaceutical aqueous formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, or a lactate salt thereof, lactic acid, a pharmaceutically acceptable beta- or gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 6 to 30 mg/ml or from 6 to less than 35 mg/ml and wherein sufficient lactic acid and pharmaceutically acceptable beta- or gamma-cyclodextrin are present to provide a clear solution.

In an embodiment of the invention is provided a pharmaceutical aqueous formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, lactic acid, a pharmaceutically acceptable beta- or gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 6 to 30 mg/ml or from 6 to less than 35 mg/ml and wherein sufficient lactic acid and pharmaceutically acceptable beta- or gamma-cyclodextrin are present to provide a clear solution.

In an embodiment of the invention is provided a pharmaceutical aqueous formulation comprising a lactate salt of 1-(4-{[4-(dimethylamino)piperidin-1-yl]carbonyl}phenyl)-3-[4-(4,6-dimorpholin-4-yl-1,3,5-triazin-2-yl)phenyl]urea, lactic acid, a pharmaceutically acceptable beta- or gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 6 to 30 mg/ml or from 6 to less than 35 mg/ml and wherein sufficient lactic acid and pharmaceutically acceptable beta- or gamma-cyclodextrin are present to provide a clear solution.

In an embodiment of the invention is provided a pharmaceutical aqueous formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, or a lactate salt thereof, lactic acid, a pharmaceutically acceptable beta- or gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 6 to 25, 6 to 20, 6 to 15, 10 to 30, 10 to 25, or 10 to 20 mg/ml and wherein sufficient lactic acid and pharmaceutically acceptable beta- or gamma-cyclodextrin are present to provide a clear solution.

In an embodiment of the invention is provided a pharmaceutical aqueous formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, lactic acid, a pharmaceutically acceptable beta- or gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 6 to 25, 6 to 20, 6 to 15, 10 to 30, 10 to 25, or 10 to 20 mg/ml and wherein sufficient lactic acid and pharmaceutically acceptable beta- or gamma-cyclodextrin are present to provide a clear solution.

In an embodiment of the invention is provided a pharmaceutical aqueous formulation comprising a lactate salt of 1-(4-{[4-(dimethylamino)piperidin-1-yl]carbonyl}phenyl)-3-[4-(4,6-dimorpholin-4-yl-1,3,5-triazin-2-yl)phenyl]urea, lactic acid, a pharmaceutically acceptable beta- or gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 6 to 25, 6 to 20, 6 to 15, 10 to 30, 10 to 25, or 10 to 20 mg/ml and wherein sufficient lactic acid and pharmaceutically acceptable beta- or gamma-cyclodextrin are present to provide a clear solution.

Preferably, for the above embodiments of the invention containing lactic acid, the pharmaceutically acceptable beta- or gamma-cyclodextrin used is 2-hydroxypropyl-beta-cyclodextrin, sulphobutylether-β-cyclodextrin (SBECD) or gamma-cyclodextrin. More preferably, the pharmaceutically acceptable beta- or gamma-cyclodextrin used is 2-hydroxypropyl-beta-cyclodextrin or gamma-cyclodextrin.

In an embodiment of the invention is provided a pharmaceutical aqueous formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, or a lactate salt thereof, lactic acid, sulphobutylether-β-cyclodextrin (SBECD) and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 6 to 25 mg/ml or from 6 to less than 30 mg/ml and wherein sufficient lactic acid and sulphobutylether-β-cyclodextrin (SBECD) are present to provide a clear solution.

In an embodiment of the invention is provided a pharmaceutical aqueous formulation 1-(4-{[4-(dimethylamino)piperidin-1-yl]carbonyl}phenyl)-3-[4-(4,6-dimorpholin-4-yl-1,3,5-triazin-2-yl)phenyl]urea, or a lactate salt thereof, lactic acid, 2-hydroxypropyl-beta-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 6 to 30 mg/ml or from 6 to less than 35 mg/ml and wherein sufficient lactic acid and 2-hydroxypropyl-beta-cyclodextrin are present to provide a clear solution.

In an embodiment of the invention is provided a pharmaceutical aqueous formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, or a lactate salt thereof, lactic acid, 2-hydroxypropyl-beta-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 6 to 30, 6 to 25, 6 to 20, 6 to 15, 10 to 30, 10 to 25, or 10 to 20 mg/ml and wherein sufficient lactic acid and 2-hydroxypropyl-beta-cyclodextrin are present to provide a clear solution.

In an embodiment of the invention is provided a pharmaceutical aqueous formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, or a lactate salt thereof, lactic acid, 2-hydroxypropyl-beta-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 6 to 30, 6 to 25, 6 to 20, 6 to 15, 10 to 30, 10 to 25, or 10 to 20 mg/ml and wherein the lactic acid concentration is from 10 to 100, 15 to 100 or 30 to 100 mM and the 2-hydroxypropyl-beta-cyclodextrin concentration is from 15 to 120, 20 to 120 or 35 to 120 mg/ml to provide a clear solution.

In an embodiment of the invention is provided a pharmaceutical aqueous formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, lactic acid, 2-hydroxypropyl-beta-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 10 to 30 or 10 to 20 mg/ml and wherein the lactic acid concentration is from 20 to 100 or 30 to 100 mM and the 2-hydroxypropyl-beta-cyclodextrin concentration is from 35 to 120 mg/ml to provide a clear solution.

In such lactic acid formulations, DL-lactic acid, D-lactic acid or L-lactic acid, or any combination thereof, may be used. Preferably, DL-lactic acid is used.

Acetic Acid Formulations

In an embodiment of the invention is provided a pharmaceutical aqueous formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, or a acetate salt thereof, acetic acid, a pharmaceutically acceptable beta- or gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 3 to 15 mg/ml or from 3 to less than 20 mg/ml and wherein sufficient acetic acid and pharmaceutically acceptable beta- or gamma-cyclodextrin are present to provide a clear solution.

In an embodiment of the invention is provided a pharmaceutical aqueous formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, acetic acid, a pharmaceutically acceptable beta- or gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 3 to 15 mg/ml or from 3 to less than 20 mg/ml and wherein sufficient acetic acid and pharmaceutically acceptable beta- or gamma-cyclodextrin are present to provide a clear solution.

In an embodiment of the invention is provided a pharmaceutical aqueous formulation comprising a acetate salt of 1-(4-{[4-(dimethylamino)piperidin-1-yl]carbonyl}phenyl)-3-[4-(4,6-dimorpholin-4-yl-1,3,5-triazin-2-yl)phenyl]urea, acetic acid, a pharmaceutically acceptable beta- or gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 3 to 15 mg/ml or from 3 to less than 20 mg/ml and wherein sufficient acetic acid and pharmaceutically acceptable beta- or gamma-cyclodextrin are present to provide a clear solution.

In an embodiment of the invention is provided a pharmaceutical aqueous formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, or a acetate salt thereof, acetic acid, a pharmaceutically acceptable beta- or gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 6 to 15, 8 to 15, or to 15 mg/ml and wherein sufficient acetic acid and pharmaceutically acceptable beta- or gamma-cyclodextrin are present to provide a clear solution.

In an embodiment of the invention is provided a pharmaceutical aqueous formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, acetic acid, a pharmaceutically acceptable beta- or gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 6 to 15, 8 to 15, or 10 to 15 mg/ml and wherein sufficient acetic acid and pharmaceutically acceptable beta- or gamma-cyclodextrin are present to provide a clear solution.

In an embodiment of the invention is provided a pharmaceutical aqueous formulation comprising a acetate salt of 1-(4-{[4-(dimethylamino)piperidin-1-yl]carbonyl}phenyl)-3-[4-(4,6-dimorpholin-4-yl-1,3,5-triazin-2-yl)phenyl]urea, acetic acid, a pharmaceutically acceptable beta- or gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 6 to 15, 8 to 15, or 10 to 15 mg/ml and wherein sufficient acetic acid and pharmaceutically acceptable beta- or gamma-cyclodextrin are present to provide a clear solution.

Preferably, for the above embodiments of the invention containing acetic acid, the pharmaceutically acceptable beta- or gamma-cyclodextrin used is 2-hydroxypropyl-beta-cyclodextrin, sulphobutylether-β-cyclodextrin (SBECD) or gamma-cyclodextrin. More preferably, the pharmaceutically acceptable beta- or gamma-cyclodextrin used is 2-hydroxypropyl-beta-cyclodextrin or sulphobutylether-β-cyclodextrin (SBECD).

Maleic Acid Formulations

In an embodiment of the invention is provided a pharmaceutical aqueous formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, or a maleate salt thereof, maleic acid, a pharmaceutically acceptable beta- or gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 3 to 30 mg/ml or from 3 to less than 35 mg/ml and wherein sufficient maleic acid and pharmaceutically acceptable beta- or gamma-cyclodextrin are present to provide a clear solution.

In an embodiment of the invention is provided a pharmaceutical aqueous formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, maleic acid, a pharmaceutically acceptable beta- or gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 3 to 30 mg/ml or from 3 to less than 35 mg/ml and wherein sufficient maleic acid and pharmaceutically acceptable beta- or gamma-cyclodextrin are present to provide a clear solution.

In an embodiment of the invention is provided a pharmaceutical aqueous formulation comprising a maleate salt of 1-(4-{[4-(dimethylamino)piperidin-1-yl]carbonyl}phenyl)-3-[4-(4,6-dimorpholin-4-yl-1,3,5-triazin-2-yl)phenyl]urea, maleic acid, a pharmaceutically acceptable beta- or gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 3 to 30 mg/ml or from 3 to less than 35 mg/ml and wherein sufficient maleic acid and pharmaceutically acceptable beta- or gamma-cyclodextrin are present to provide a clear solution.

In an embodiment of the invention is provided a pharmaceutical aqueous formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, or a maleate salt thereof, maleic acid, a pharmaceutically acceptable beta- or gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 4 to 25, 4 to 20, 4 to 15, 6 to 25, 6 to 20, 6 to 15, 10 to 30, 10 to 25, or 10 to 20 mg/ml and wherein sufficient maleic acid and pharmaceutically acceptable beta- or gamma-cyclodextrin are present to provide a clear solution.

In an embodiment of the invention is provided a pharmaceutical aqueous formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, maleic acid, a pharmaceutically acceptable beta- or gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 4 to 25, 4 to 20, 4 to 15, 6 to 25, 6 to 20, 6 to 15, 10 to 30, 10 to 25, or 10 to 20 mg/ml and wherein sufficient maleic acid and pharmaceutically acceptable beta- or gamma-cyclodextrin are present to provide a clear solution.

In an embodiment of the invention is provided a pharmaceutical aqueous formulation comprising a maleate salt of 1-(4-{[4-(dimethylamino)piperidin-1-yl]carbonyl}phenyl)-3-[4-(4,6-dimorpholin-4-yl-1,3,5-triazin-2-yl)phenyl]urea, maleic acid, a pharmaceutically acceptable beta- or gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 4 to 25, 4 to 20, 4 to 15, 6 to 25, 6 to 20, 6 to 15, 10 to 30, 10 to 25, or 10 to 20 mg/ml and wherein sufficient maleic acid and pharmaceutically acceptable beta- or gamma-cyclodextrin are present to provide a clear solution.

Preferably, for the above embodiments of the invention containing maleic acid, the pharmaceutically acceptable beta- or gamma-cyclodextrin used is 2-hydroxypropyl-beta-cyclodextrin, sulphobutylether-β-cyclodextrin (SBECD) or gamma-cyclodextrin. More preferably, the pharmaceutically acceptable beta- or gamma-cyclodextrin used is 2-hydroxypropyl-beta-cyclodextrin or gamma-cyclodextrin.

In an embodiment of the invention is provided a pharmaceutical aqueous formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, or a maleate salt thereof, maleic acid, hydroxypropyl-beta-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 3 to 20 mg/ml or from 3 to less than 25 mg/ml and wherein sufficient maleic acid and hydroxypropyl-beta-cyclodextrin are present to provide a clear solution.

In an embodiment of the invention is provided a pharmaceutical aqueous formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, or a maleate salt thereof, maleic acid, gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 3 to 15 mg/ml or from 3 to less than 20 mg/ml and wherein sufficient maleic acid and gamma-cyclodextrin are present to provide a clear solution.

Succinic Acid Formulations

In an embodiment of the invention is provided a pharmaceutical aqueous formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, or a succinate salt thereof, succinic acid, a pharmaceutically acceptable beta- or gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 3 to 65 mg/ml or from 3 to less than 70 mg/ml and wherein sufficient succinic acid and pharmaceutically acceptable beta- or gamma-cyclodextrin are present to provide a clear solution.

In an embodiment of the invention is provided a pharmaceutical aqueous formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, succinic acid, a pharmaceutically acceptable beta- or gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 3 to 65 mg/ml or from 3 to less than 70 mg/ml and wherein sufficient succinic acid and pharmaceutically acceptable beta- or gamma-cyclodextrin are present to provide a clear solution.

In an embodiment of the invention is provided a pharmaceutical aqueous formulation comprising a succinate salt of 1-(4-{[4-(dimethylamino)piperidin-1-yl]carbonyl}phenyl)-3-[4-(4,6-dimorpholin-4-yl-1,3,5-triazin-2-yl)phenyl]urea, succinic acid, a pharmaceutically acceptable beta- or gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 3 to 65 mg/ml or from 3 to less than 70 mg/ml and wherein sufficient succinic acid and pharmaceutically acceptable beta- or gamma-cyclodextrin are present to provide a clear solution.

In an embodiment of the invention is provided a pharmaceutical aqueous formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, or a succinate salt thereof, succinic acid, a pharmaceutically acceptable beta- or gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 4 to 25, 4 to 20, 4 to 15, 6 to 25, 6 to 20, 6 to 15, 10 to 30, 10 to 25, or 10 to 20 mg/ml and wherein sufficient succinic acid and pharmaceutically acceptable beta- or gamma-cyclodextrin are present to provide a clear solution.

In an embodiment of the invention is provided a pharmaceutical aqueous formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, succinic acid, a pharmaceutically acceptable beta- or gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 4 to 25, 4 to 20, 4 to 15, 6 to 25, 6 to 20, 6 to 15, 10 to 30, 10 to 25, or 10 to 20 mg/ml and wherein sufficient succinic acid and pharmaceutically acceptable beta- or gamma-cyclodextrin are present to provide a clear solution.

In an embodiment of the invention is provided a pharmaceutical aqueous formulation comprising a succinate salt of 1-(4-{[4-(dimethylamino)piperidin-1-yl]carbonyl}phenyl)-3-[4-(4,6-dimorpholin-4-yl-1,3,5-triazin-2-yl)phenyl]urea, succinic acid, a pharmaceutically acceptable beta- or gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 4 to 25, 4 to 20, 4 to 15, 6 to 25, 6 to 20, 6 to 15, 10 to 30, 10 to 25, or 10 to 20 mg/ml and wherein sufficient succinic acid and pharmaceutically acceptable beta- or gamma-cyclodextrin are present to provide a clear solution.

Preferably, for the above embodiments of the invention containing succinic acid, the pharmaceutically acceptable beta- or gamma-cyclodextrin used is 2-hydroxypropyl-beta-cyclodextrin, sulphobutylether-β-cyclodextrin (SBECD) or gamma-cyclodextrin. More preferably, the pharmaceutically acceptable beta- or gamma-cyclodextrin used is 2-hydroxypropyl-beta-cyclodextrin or gamma-cyclodextrin.

In an embodiment of the invention is provided a pharmaceutical aqueous formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, or a succinate salt thereof, succinic acid, hydroxypropyl-beta-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 3 to 25 mg/ml or from 3 to less than 30 mg/ml and wherein sufficient succinic acid and hydroxypropyl-beta-cyclodextrin are present to provide a clear solution.

In an embodiment of the invention is provided a pharmaceutical aqueous formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, or a succinate salt thereof, succinic acid, sulphobutylether-β-cyclodextrin (SBECD) and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 3 to 20 mg/ml or from 3 to less than 25 mg/ml and wherein sufficient succinic acid and sulphobutylether-β-cyclodextrin (SBECD) are present to provide a clear solution.

Citric Acid Formulations

In an embodiment of the invention is provided a pharmaceutical aqueous formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, or a citrate salt thereof, citric acid, a pharmaceutically acceptable beta- or gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 3 to 55 mg/ml or from 3 to less than 60 mg/ml and wherein sufficient citric acid and pharmaceutically acceptable beta- or gamma-cyclodextrin are present to provide a clear solution.

In an embodiment of the invention is provided a pharmaceutical aqueous formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, citric acid, a pharmaceutically acceptable beta- or gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 3 to 55 mg/ml or from 3 to less than 60 mg/ml and wherein sufficient citric acid and pharmaceutically acceptable beta- or gamma-cyclodextrin are present to provide a clear solution.

In an embodiment of the invention is provided a pharmaceutical aqueous formulation comprising a citrate salt of 1-(4-{[4-(dimethylamino)piperidin-1-yl]carbonyl}phenyl)-3-[4-(4,6-dimorpholin-4-yl-1,3,5-triazin-2-yl)phenyl]urea, citric acid, a pharmaceutically acceptable beta- or gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 3 to 55 mg/ml or from 3 to less than 60 mg/ml and wherein sufficient citric acid and pharmaceutically acceptable beta- or gamma-cyclodextrin are present to provide a clear solution.

In an embodiment of the invention is provided a pharmaceutical aqueous formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, or a citrate salt thereof, citric acid, a pharmaceutically acceptable beta- or gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 4 to 25, 4 to 20, 4 to 15, 6 to 25, 6 to 20, 6 to 15, 4 to 30, 6 to 30, 10 to 30, 10 to 25, or 10 to 20 mg/ml and wherein sufficient citric acid and pharmaceutically acceptable beta- or gamma-cyclodextrin are present to provide a clear solution.

In an embodiment of the invention is provided a pharmaceutical aqueous formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, citric acid, a pharmaceutically acceptable beta- or gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 4 to 25, 4 to 20, 4 to 15, 6 to 25, 6 to 20, 6 to 15, 4 to 30, 6 to 30, 10 to 30, 10 to 25, or 10 to 20 mg/ml and wherein sufficient citric acid and pharmaceutically acceptable beta- or gamma-cyclodextrin are present to provide a clear solution.

In an embodiment of the invention is provided a pharmaceutical aqueous formulation comprising a citrate salt of 1-(4-{[4-(dimethylamino)piperidin-1-yl]carbonyl}phenyl)-3-[4-(4,6-dimorpholin-4-yl-1,3,5-triazin-2-yl)phenyl]urea, citric acid, a pharmaceutically acceptable beta- or gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 4 to 25, 4 to 20, 4 to 15, 6 to 25, 6 to 20, 6 to 15, 4 to 30, 6 to 30, 10 to 30, 10 to 25, or 10 to 20 mg/ml and wherein sufficient citric acid and pharmaceutically acceptable beta- or gamma-cyclodextrin are present to provide a clear solution.

Preferably, for the above embodiments of the invention containing citric acid, the pharmaceutically acceptable beta- or gamma-cyclodextrin used is 2-hydroxypropyl-beta-cyclodextrin, sulphobutylether-β-cyclodextrin (SBECD) or gamma-cyclodextrin. More preferably, the pharmaceutically acceptable beta- or gamma-cyclodextrin used is 2-hydroxypropyl-beta-cyclodextrin or gamma-cyclodextrin.

In an embodiment of the invention is provided a pharmaceutical aqueous formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, or a citrate salt thereof, citric acid, hydroxypropyl-beta-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 3 to 25 mg/ml or from 3 to less than 30 mg/ml and wherein sufficient citric acid and hydroxypropyl-beta-cyclodextrin are present to provide a clear solution.

In an embodiment of the invention is provided a pharmaceutical aqueous formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, or a citrate salt thereof, citric acid, sulphobutylether-β-cyclodextrin (SBECD) and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 3 to 20 mg/ml or from 3 to less than 25 mg/ml and wherein sufficient citric acid and sulphobutylether-β-cyclodextrin (SBECD) are present to provide a clear solution.

Malic Acid Formulations

In an embodiment of the invention is provided a pharmaceutical aqueous formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, or a malate salt thereof, malic acid, a pharmaceutically acceptable beta- or gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 3 to 65 mg/ml or from 3 to less than 70 mg/ml and wherein sufficient malic acid and pharmaceutically acceptable beta- or gamma-cyclodextrin are present to provide a clear solution.

In an embodiment of the invention is provided a pharmaceutical aqueous formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, malic acid, a pharmaceutically acceptable beta- or gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 3 to 65 mg/ml or from 3 to less than 70 mg/ml and wherein sufficient malic acid and pharmaceutically acceptable beta- or gamma-cyclodextrin are present to provide a clear solution.

In an embodiment of the invention is provided a pharmaceutical aqueous formulation comprising a malate salt of 1-(4-{[4-(dimethylamino)piperidin-1-yl]carbonyl}phenyl)-3-[4-(4,6-dimorpholin-4-yl-1,3,5-triazin-2-yl)phenyl]urea, malic acid, a pharmaceutically acceptable beta- or gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 3 to 65 mg/ml or from 3 to less than 70 mg/ml and wherein sufficient malic acid and pharmaceutically acceptable beta- or gamma-cyclodextrin are present to provide a clear solution.

In an embodiment of the invention is provided a pharmaceutical aqueous formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, or a malate salt thereof, malic acid, a pharmaceutically acceptable beta- or gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 4 to 25, 4 to 20, 4 to 15, 6 to 25, 6 to 20, 6 to 15, 4 to 30, 6 to 30, 10 to 30, 10 to 25, or 10 to 20 mg/ml and wherein sufficient malic acid and pharmaceutically acceptable beta- or gamma-cyclodextrin are present to provide a clear solution.

In an embodiment of the invention is provided a pharmaceutical aqueous formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, malic acid, a pharmaceutically acceptable beta- or gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 4 to 25, 4 to 20, 4 to 15, 6 to 25, 6 to 20, 6 to 15, 4 to 30, 6 to 30, 10 to 30, 10 to 25, or 10 to 20 mg/ml and wherein sufficient malic acid and pharmaceutically acceptable beta- or gamma-cyclodextrin are present to provide a clear solution.

In an embodiment of the invention is provided a pharmaceutical aqueous formulation comprising a malate salt of 1-(4-{[4-(dimethylamino)piperidin-1-yl]carbonyl}phenyl)-3-[4-(4,6-dimorpholin-4-yl-1,3,5-triazin-2-yl)phenyl]urea, malic acid, a pharmaceutically acceptable beta- or gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 4 to 25, 4 to 20, 4 to 15, 6 to 25, 6 to 20, 6 to 15, 4 to 30, 6 to 30, 10 to 30, 10 to 25, or 10 to 20 mg/ml and wherein sufficient malic acid and pharmaceutically acceptable beta- or gamma-cyclodextrin are present to provide a clear solution.

Preferably, for the above embodiments of the invention containing malic acid, the pharmaceutically acceptable beta- or gamma-cyclodextrin used is 2-hydroxypropyl-beta-cyclodextrin, sulphobutylether-β-cyclodextrin (SBECD) or gamma-cyclodextrin. More preferably, the pharmaceutically acceptable beta- or gamma-cyclodextrin used is 2-hydroxypropyl-beta-cyclodextrin or gamma-cyclodextrin.

In an embodiment of the invention is provided a pharmaceutical aqueous formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, or a malate salt thereof, malic acid, hydroxypropyl-beta-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 3 to 30 mg/ml or from 3 to less than 35 mg/ml and wherein sufficient malic acid and hydroxypropyl-beta-cyclodextrin are present to provide a clear solution.

In an embodiment of the invention is provided a pharmaceutical aqueous formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, or a malate salt thereof, malic acid, sulphobutylether-β-cyclodextrin (SBECD) and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 3 to 25 mg/ml or from 3 to less than 30 mg/ml and wherein sufficient malic acid and sulphobutylether-β-cyclodextrin (SBECD) are present to provide a clear solution.

Tartaric Acid Formulations

In an embodiment of the invention is provided a pharmaceutical aqueous formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, or a tartrate salt thereof, tartaric acid, a pharmaceutically acceptable beta- or gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 3 to 65 mg/ml or from 3 to less than 70 mg/ml and wherein sufficient tartaric acid and pharmaceutically acceptable beta- or gamma-cyclodextrin are present to provide a clear solution.

In an embodiment of the invention is provided a pharmaceutical aqueous formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, tartaric acid, a pharmaceutically acceptable beta- and or gamma-cyclodextrin water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 3 to 65 mg/ml or from 3 to less than 70 mg/ml and wherein sufficient tartaric acid and pharmaceutically acceptable beta- or gamma-cyclodextrin are present to provide a clear solution.

In an embodiment of the invention is provided a pharmaceutical aqueous formulation comprising a tartrate salt of 1-(4-{[4-(dimethylamino)piperidin-1-yl]carbonyl}phenyl)-3-[4-(4,6-dimorpholin-4-yl-1,3,5-triazin-2-yl)phenyl]urea, tartaric acid, a pharmaceutically acceptable beta- or gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 3 to 65 mg/ml or from 3 to less than 70 mg/ml and wherein sufficient tartaric acid and pharmaceutically acceptable beta- or gamma-cyclodextrin are present to provide a clear solution.

In an embodiment of the invention is provided a pharmaceutical aqueous formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, or a tartrate salt thereof, tartaric acid, a pharmaceutically acceptable beta- or gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 4 to 25, 4 to 20, 4 to 15, 6 to 25, 6 to 20, 6 to 15, 4 to 30, 6 to 30, 10 to 30, 10 to 25, or 10 to 20 mg/ml and wherein sufficient tartaric acid and pharmaceutically acceptable beta- or gamma-cyclodextrin are present to provide a clear solution.

In an embodiment of the invention is provided a pharmaceutical aqueous formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, tartaric acid, a pharmaceutically acceptable beta-water, or gamma-cyclodextrin and wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 4 to 25, 4 to 20, 4 to 15, 6 to 25, 6 to 20, 6 to 15, 4 to 30, 6 to 30, 10 to 30, 10 to 25, or 10 to 20 mg/ml and wherein sufficient tartaric acid and pharmaceutically acceptable beta- or gamma-cyclodextrin are present to provide a clear solution.

In an embodiment of the invention is provided a pharmaceutical aqueous formulation comprising a tartrate salt of 1-(4-{[4-(dimethylamino)piperidin-1-yl]carbonyl}phenyl)-3-[4-(4,6-dimorpholin-4-yl-1,3,5-triazin-2-yl)phenyl]urea, tartaric acid, a pharmaceutically acceptable beta- or gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 4 to 25, 4 to 20, 4 to 15, 6 to 25, 6 to 20, 6 to 15, 4 to 30, 6 to 30, 10 to 30, 10 to 25, or 10 to 20 mg/ml and wherein sufficient tartaric acid and pharmaceutically acceptable beta- or gamma-cyclodextrin are present to provide a clear solution.

Preferably, for the above embodiments of the invention containing tartaric acid, the pharmaceutically acceptable beta- or gamma-cyclodextrin used is 2-hydroxypropyl-beta-cyclodextrin, sulphobutylether-β-cyclodextrin (SBECD) or gamma-cyclodextrin. More preferably, the pharmaceutically acceptable beta- or gamma-cyclodextrin used is 2-hydroxypropyl-beta-cyclodextrin or gamma-cyclodextrin.

In an embodiment of the invention is provided a pharmaceutical aqueous formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, or a tartrate salt thereof, tartaric acid, hydroxypropyl-beta-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 3 to 30 mg/ml or from 3 to less than 35 mg/ml and wherein sufficient tartaric acid and hydroxypropyl-beta-cyclodextrin are present to provide a clear solution.

In an embodiment of the invention is provided a pharmaceutical aqueous formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, or a tartrate salt thereof, tartaric acid, sulphobutylether-β-cyclodextrin (SBECD) and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 3 to 25 mg/ml or from 3 to less than 30 mg/ml and wherein sufficient tartaric acid and sulphobutylether-β-cyclodextrin (SBECD) are present to provide a clear solution.

Hydrochloric Acid Formulations

In an embodiment of the invention is provided a pharmaceutical aqueous formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, or a hydrochloride salt thereof, hydrochloric acid, a pharmaceutically acceptable beta- or gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 3 to 60 mg/ml or from 3 to less than 65 mg/ml and wherein sufficient hydrochloric acid and pharmaceutically acceptable beta- or gamma-cyclodextrin are present to provide a clear solution.

In an embodiment of the invention is provided a pharmaceutical aqueous formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, hydrochloric acid, a pharmaceutically acceptable beta- or gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 3 to 60 mg/ml or from 3 to less than 65 mg/ml and wherein sufficient hydrochloric acid and pharmaceutically acceptable beta- or gamma-cyclodextrin are present to provide a clear solution.

In an embodiment of the invention is provided a pharmaceutical aqueous formulation comprising a hydrochloride salt of 1-(4-{[4-(dimethylamino)piperidin-1-yl]carbonyl}phenyl)-3-[4-(4,6-dimorpholin-4-yl-1,3,5-triazin-2-yl)phenyl]urea, hydrochloric acid, a pharmaceutically acceptable beta- or gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 3 to 60 mg/ml or from 3 to less than 65 mg/ml and wherein sufficient hydrochloric acid and pharmaceutically acceptable beta- or gamma-cyclodextrin are present to provide a clear solution.

In an embodiment of the invention is provided a pharmaceutical aqueous formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, or a hydrochloride salt thereof, hydrochloric acid, a pharmaceutically acceptable beta- or gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 4 to 25, 4 to 20, 4 to 15, 6 to 25, 6 to 20, 6 to 15, 4 to 30, 6 to 30, 10 to 30, 10 to 35, 10 to 25, or 10 to 20 mg/ml and wherein sufficient hydrochloric acid and pharmaceutically acceptable beta- or gamma-cyclodextrin are present to provide a clear solution.

In an embodiment of the invention is provided a pharmaceutical aqueous formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, hydrochloric acid, a pharmaceutically acceptable beta- or gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 4 to 25, 4 to 20, 4 to 15, 6 to 25, 6 to 20, 6 to 15, 4 to 30, 6 to 30, 10 to 30, 10 to 35, 10 to 25, or 10 to 20 mg/ml and wherein sufficient hydrochloric acid and pharmaceutically acceptable beta- or gamma-cyclodextrin are present to provide a clear solution.

In an embodiment of the invention is provided a pharmaceutical aqueous formulation comprising a hydrochloride salt of 1-(4-{[4-(dimethylamino)piperidin-1-yl]carbonyl}phenyl)-3-[4-(4,6-dimorpholin-4-yl-1,3,5-triazin-2-yl)phenyl]urea, hydrochloric acid, a pharmaceutically acceptable beta- or gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 4 to 25, 4 to 20, 4 to 15, 6 to 25, 6 to 20, 6 to 15, 4 to 30, 6 to 30, 10 to 30, 10 to 35, 10 to 25, or 10 to 20 mg/ml and wherein sufficient hydrochloric acid and pharmaceutically acceptable beta- or gamma-cyclodextrin are present to provide a clear solution.

Preferably, for the above embodiments of the invention containing hydrochloric acid, the pharmaceutically acceptable beta- or gamma-cyclodextrin used is 2-hydroxypropyl-beta-cyclodextrin, sulphobutylether-β-cyclodextrin (SBECD) or gamma-cyclodextrin. More preferably, the pharmaceutically acceptable beta- or gamma-cyclodextrin used is 2-hydroxypropyl-beta-cyclodextrin or gamma-cyclodextrin.

In an embodiment of the invention is provided a pharmaceutical aqueous formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, or a hydrochloride salt thereof, hydrochloric acid, hydroxypropyl-beta-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 3 to 35 mg/ml or from 3 to less than 40 mg/ml and wherein sufficient hydrochloric acid and hydroxypropyl-beta-cyclodextrin are present to provide a clear solution.

In an embodiment of the invention is provided a pharmaceutical aqueous formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, or a hydrochloride salt thereof, hydrochloric acid, sulphobutylether-β-cyclodextrin (SBECD) and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 3 to 30 mg/ml or from 3 to less than 35 mg/ml and wherein sufficient hydrochloric acid and sulphobutylether-β-cyclodextrin (SBECD) are present to provide a clear solution.

Orthophosphoric Acid Formulations

In an embodiment of the invention is provided a pharmaceutical aqueous formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, or a phosphate salt thereof, orthophosphoric acid, a pharmaceutically acceptable beta- or gamma-cyclodextrin and water, wherein 1-(4-{[4-(dimethylamino)piperidin-1-yl]carbonyl}phenyl)-3-[4-(4,6-morpholin-4-yl-1,3,5-triazin-2-yl)phenyl]urea is present at a solution concentration of from 4 to 50 mg/ml or from 4 to less than 55 mg/ml and wherein sufficient orthophosphoric acid and pharmaceutically acceptable beta- or gamma-cyclodextrin are present to provide a clear solution.

In an embodiment of the invention is provided a pharmaceutical aqueous formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, orthophosphoric acid, a pharmaceutically acceptable beta- or gamma-cyclodextrin and water, wherein 1-(4-{[4-(dimethylamino)piperidin-1-yl]carbonyl}phenyl)-3-[4-(4,6-morpholin-4-yl-1,3,5-triazin-2-yl)phenyl]urea is present at a solution concentration of from 4 to 50 mg/ml or from 4 to less than 55 mg/ml and wherein sufficient orthophosphoric acid and pharmaceutically acceptable beta- or gamma-cyclodextrin are present to provide a clear solution.

In an embodiment of the invention is provided a pharmaceutical aqueous formulation comprising a phosphate salt of 1-(4-{[4-(dimethylamino)piperidin-1-yl]carbonyl}phenyl)-3-[4-(4,6-dimorpholin-4-yl-1,3,5-triazin-2-yl)phenyl]urea, orthophosphoric acid, a pharmaceutically acceptable beta- or gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 4 to 50 mg/ml or from 4 to less than 55 mg/ml and wherein sufficient orthophosphoric acid and pharmaceutically acceptable beta- or gamma-cyclodextrin are present to provide a clear solution.

In an embodiment of the invention is provided a pharmaceutical aqueous formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, or a phosphate salt thereof, orthophosphoric acid, a pharmaceutically acceptable beta- or gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 4 to 25, 4 to 20, 4 to 15, 6 to 25, 6 to 20, 6 to 15, 4 to 30, 6 to 30, 10 to 30, 10 to 35, 10 to 25, or 10 to 20 mg/ml and wherein sufficient orthophosphoric acid and pharmaceutically acceptable beta- or gamma-cyclodextrin are present to provide a clear solution.

In an embodiment of the invention is provided a pharmaceutical aqueous formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, orthophosphoric acid, a pharmaceutically acceptable beta- or gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 4 to 25, 4 to 20, 4 to 15, 6 to 25, 6 to 20, 6 to 15, 4 to 30, 6 to 30, 10 to 30, 10 to 35, 10 to 25, or 10 to 20 mg/ml and wherein sufficient orthophosphoric acid and pharmaceutically acceptable beta- or gamma-cyclodextrin are present to provide a clear solution.

In an embodiment of the invention is provided a pharmaceutical aqueous formulation comprising a phosphate salt of 1-(4-{[4-(dimethylamino)piperidin-1-yl]carbonyl}phenyl)-3-[4-(4,6-dimorpholin-4-yl-1,3,5-triazin-2-yl)phenyl]urea, orthophosphoric acid, a pharmaceutically acceptable beta- or gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 4 to 25, 4 to 20, 4 to 15, 6 to 25, 6 to 20, 6 to 15, 4 to 30, 6 to 30, 10 to 30, 10 to 35, 10 to 25, or 10 to 20 mg/ml and wherein sufficient orthophosphoric acid and pharmaceutically acceptable beta- or gamma-cyclodextrin are present to provide a clear solution.

Preferably, for the above embodiments of the invention containing orthophosphoric acid, the pharmaceutically acceptable beta- or gamma-cyclodextrin used is 2-hydroxypropyl-beta-cyclodextrin, sulphobutylether-β-cyclodextrin (SBECD) or gamma-cyclodextrin. More preferably, the pharmaceutically acceptable beta- or gamma-cyclodextrin used is 2-hydroxypropyl-beta-cyclodextrin or gamma-cyclodextrin.

In an embodiment of the invention is provided a pharmaceutical aqueous formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, or a phosphate salt thereof, orthophosphoric acid, hydroxypropyl-beta-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 4 to 35 mg/ml or from 4 to less than 40 mg/ml and wherein sufficient orthophosphoric acid and hydroxypropyl-beta-cyclodextrin are present to provide a clear solution.

In an embodiment of the invention is provided a pharmaceutical aqueous formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, or a phosphate salt thereof, orthophosphoric acid, sulphobutylether-β-cyclodextrin (SBECD) and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 4 to 30 mg/ml or from 4 to less than 35 mg/ml and wherein sufficient orthophosphoric acid and sulphobutylether-β-cyclodextrin (SBECD) are present to provide a clear solution.

The "solution concentration" values referred to herein relate to the concentration of the free base of 1-(4-{[4-(dimethylamino)piperidin-1-yl]carbonyl}phenyl)-3-[4-(4,6-dimorpholin-4-yl-1,3,5-triazin-2-yl)phenyl]urea in the formulation of the invention.

The formulations of the invention can be directly administered to the patient (in order to avoid degradation occurring), intravenously or parenterally, preferably with the addition of a tonicity modifier. Alternatively, for administration to a patient at a later date, such a formulation, optionally containing a bulking agent and/or tonicity modifier, may be first freeze-dried to prepare a lyophilised solid composition that is chemically stable on storage (preferably at least 2 years), and which lyophilised solid composition then can be constituted, or reconstituted, to provide a clear aqueous solution, preferably with the addition of a tonicity modifier, as necessary, immediately prior to administration to a patient by the intravenous (or parenteral) route. The reconstituted or constituted solution may be added to an infusion bag prior to administration to a patient.

The preferred concentration of pharmaceutically acceptable organic or inorganic acid for use in a formulation of the invention is from 10 to 200 mM or from 50 to 200 mM, and preferably is about 50 mM, about 100 mM or about 150 mM.

Preferably, the concentration of pharmaceutically acceptable organic or inorganic acid is about 100 mM.

The preferred amount of pharmaceutically acceptable beta- or gamma-cyclodextrin for use in a formulation of the invention is from 2 to 30% w/v, from 5 to 20% w/v, or from 15 to 30% w/v, and preferably is about 20% w/v or about 25% w/v. Preferably, the amount of pharmaceutically acceptable beta- or gamma-cyclodextrin for use in a formulation of the invention is about 20% w/v.

If the formulation of the invention is to be freeze-dried to provide a lyophilised solid composition, a bulking agent may be added to the formulation prior to the freeze-drying process commencing. The primary function of the bulking agent is to provide the freeze-dried solid with a non-collapsible, structural integrity that will allow rapid reconstitution on constitution of the aqueous formulation prior to administration, and it should also facilitate efficient lyophilisation. Bulking agents are typically used when the total mass of solutes in the formulation is less than 2 g/100 ml. Bulking agents may also be added to achieve isotonicity with blood. The bulking agent may be selected from a saccharide, sugar alcohol, amino acid or polymer, or be a mixture of two or more of any thereof. Preferably, the bulking agent is a sugar or sugar alcohol, or a mixture thereof. Preferably, the sugar is sucrose. Preferably, the sugar alcohol is mannitol.

Preferably, from 5 to 10% w/v of a bulking agent is used, if present.

Reconstitution of the lyophilised solid composition may be achieved by addition of the requisite quantity of water that was present prior to lyophilisation in order that a clear solution is obtained. A tonicity modifier may then be added prior to use.

Constitution of the lyophilised solid composition may be achieved using an appropriate quantity of water and/or an aqueous solution of a suitable tonicity modifier in order to ensure that a clear solution is obtained.

A tonicity modifier may be present prior to intravenous or parenteral administration of the formulation to a patient by injection to avoid crenation or hemolysis of red blood cells, and to mitigate or avoid pain and discomfort to the patient. This requires that the formulation to be administered to the patient has an effective osmotic pressure that is approximately the same as that of the blood of the patient.

Suitable tonicity modifiers are non-ionic tonicity modifiers such as glycerol, sorbitol, mannitol, sucrose, propylene glycol or dextrose, or a mixture of any 2 or more thereof. Preferably the non-ionic tonicity modifier is dextrose, sucrose or mannitol, or is a mixture of any 2 or more thereof.

Preferably, from 1 to 5% w/v of a tonicity modifier is used.

Aqueous pharmaceutical formulations of the invention that are suitable for intravenous administration generally have a pH of from 3 to 9. However, lower pH values are tolerated in certain settings. Preferably, the pH is from 3 to 8 or from 4 to 8.

The formulation of the invention may be used for the curative, palliative or prophylactic treatment of cancer in a mammal, including a human being. The cancer to be treated may be selected from the group consisting of leukemia, skin cancer, bladder cancer, breast cancer, uterus cancer, ovary cancer, prostate cancer, lung cancer, colon cancer, pancreas cancer, renal cancer, gastric cancer and brain cancer.

The weekly dose of 1-(4-{[4-(dimethylamino)piperidin-1-yl]carbonyl}phenyl)-3-[4-(4,6-dimorpholin-4-yl-1,3,5-triazin-2-yl)phenyl]urea to be administered by the intravenous route for the treatment of cancer using the formulations disclosed herein is preferably in the range of from 100 to 400 mg per week.

The following Examples describe the preparation of the formulations of the invention.

Example 1

Preparation of a Pharmaceutical Aqueous Solution Formulation Comprising 35 mg/ml of 1-(4-{[4-(dimethylamino)piperidin-1-yl]carbonyl}phenyl)-3-[4 (4,6-dimorpholin-4-yl-1,3,5-triazin-2-yl)phenyl]urea, 20% w/v 2-hydroxypropyl-beta-cyclodextrin and Hydrochloric Acid Hydrochloric acid (1M aqueous solution) (10 ml, 100 mM) was diluted with water for irrigation (80 ml). 2-Hydroxypropyl-beta-cyclodextrin (93% w/w adjusted potency) (21.57 g, 147.2 mM) was added and the solution was stirred until a particle-free solution was achieved. 1-(4-{[4-(Dimethylamino)piperidin-1-yl]carbonyl}phenyl)-3-[4-(4,6-dimorpholin-4-yl-1,3,5-triazin-2-yl)phenyl]urea (3500 mg, 56.9 mM) was added to the solution and stirred until a particle-free solution was achieved. Water for irrigation was added with stirring to achieve a target volume of 100 ml.

(i) Visual Analysis

A sample of the formulation was analysed in accordance with the visual method defined in European Pharmacopoeia Method 2.9.20 (using a Verivide (trade mark) light cabinet and a light meter reading of 3250 lux against a matt black panel and a white panel) to determine if crystallites or particles were present. The sample was tested by this method both when the solution was first made up and then 24 hours thereafter.

(ii) OPM Analysis

A sample of the formulation was placed on a clean glass microscopy slide and covered with a glass cover slip. It was then analysed by OPM using both non-polarised and cross-polarised light under a Nikon LV 100POL (trade mark) microscope with a 10× magnification lens and a 10× magnification eyepiece to determine if crystallites or particles were present. The image was recorded using a DFK 23UP031 TIS USB 3.0 CMOS (trade mark) Colour Industrial Camera 5MP 1/2,5" and image capture software. The procedure was also repeated using a sample of the formulation in a glass capillary tube. The sample was tested by this method when the solution was first made up, and then at 4 and 24 hours thereafter.

Example 2

Preparation of a Pharmaceutical Aqueous Solution Formulation Comprising 30 mg/ml of 1-(4-{[4-(dimethylamino)piperidin-1-yl]carbonyl}phenyl)-3-[4-(4,6-dimorpholin-4-yl-1,3,5-triazin-2-yl)phenyl]urea, 20% w/v sulphobutylether-beta-cyclodextrin (SBECD) and Tartaric Acid Tartaric acid (racemic) (99% w/w potency) (1.5 g, 100 mM) was diluted with water for irrigation (80 ml). Sulphobutylether-beta-cyclodextrin (90% w/w adjusted potency) (22.18 g, 195 mM) was added and the solution was stirred until a particle-free solution was achieved. 1-(4-{[4-(Dimethylamino)piperidin-1-yl]carbonyl}phenyl)-3-[4-(4,6-dimorpholin-4-yl-1,3,5-triazin-2-yl)phenyl]urea (3000 mg, 48.7 mM) was added to the solution and stirred until a particle-free solution was achieved. Water for irrigation was added with stirring to achieve target volume of 100 ml.

Samples of the formulation were analysed in accordance with the methods of Example 1.

Example 3

Preparation of a Pharmaceutical Aqueous Solution Formulation Comprising 45 mg/ml of 1-(4-{[4-(dimethylamino)piperidin-1-yl]carbonyl}phenyl)-3-[4 (4,6-dimorpholin-4-yl-1,3,5-triazin-2-yl)phenyl]urea, 20% w/v Gamma-Cyclodextrin and Orthophosphoric Acid Orthophosphoric acid (99% w/w assumed potency) (979 mg, 100 mM) was diluted with water for irrigation (80 ml). Gamma-cyclodextrin (assumed 100% potency) (20 g, 154 mM) was added and the solution was stirred until a particle-free solution was achieved. 1-(4-{[4-(Dimethylamino)piperidin-1-yl]carbonyl}phenyl)-3-[4-(4,6-dimorpholin-4-yl-1,3,5-triazin-2-yl)phenyl]urea (4500 mg, 73.1 mM) was added to the solution and stirred until a particle-free solution was achieved. Water for irrigation was added with stirring to achieve target volume of 100 ml.

Samples of the formulation were analysed in accordance with the methods of Example 1.

Example 4

Preparation of a Lyophilised Composition of a Pharmaceutical Aqueous Solution Formulation of the Invention A pharmaceutical aqueous solution formulation of the invention (e.g. prepared in accordance with any one of Examples 1-3) is filled into 10 ml vials to a target volume of 3 ml. The vials are partially stoppered (not sealed) with a 20 mm Gray Lyo D777-1 V10-F597W FluroTec Siliconised (trade mark) stopper. The vials are loaded into stainless steel trays and inserted into a LSL1000 (trade mark) freeze dryer. The shelf temperature was set at 5° C. The freeze drying cycle is then run in accordance with conventional procedures.

On completion of the freeze drying cycle the freeze dryer is back-filled with sterile filtered nitrogen to a set point of 500 Torr (ca. 666 mbar or 66,600 Pascals), and the vials are fully closed using the stoppers. The freeze dryer is then vented to atmospheric pressure using sterile filtered air and the vials are unloaded from the freeze dryer.

Each vial contains the freeze dried (lyophilised) formulation as a solid.

Example 5

Reconstitution of a Pharmaceutical Aqueous Solution Formulation of the Invention from a Lyophilised Solid Composition of the Invention A vial of lyophilised solid composition prepared in Example 4 is reconstituted as follows. Water for irrigation (3 ml) is injected using a syringe into the vial containing the lyophilised composition prepared in Example 4. The mixture is swirled until a particle-free solution was obtained.

Example 6

Preparation of a Lyophilised Composition of a Pharmaceutical Aqueous Solution Formulation Comprising 10 mg/ml of 1-(4-{[4-(dimethylamino) piperidin-1-yl]carbonyl}phenyl)-3-[4-(4,6-dimorpholin-4-yl-1,3,5-triazin-2-yl)phenyl]urea, 5% w/v 2-hydroxypropyl-beta-cyclodextrin and Lactic Acid DL-lactic acid (4.505 g, 30 mM) was diluted with water for irrigation (1275 mL). 2-Hydroxypropyl-beta-cyclodextrin (92.85% w/w adjusted potency) (80.775 g, 35.7 mM) was added and the solution was stirred until a particle-free solution was achieved. 1-(4-{[4-(Dimethylamino)piperidin-1-yl]carbonyl}phenyl)-3-[4-(4,6-dimorpholin-4-yl-1,3,5-triazin-2-yl)phenyl]urea (15.00 g, 16.24 mM) was added to the solution and stirred until a particle-free solution was achieved. Water for irrigation was added with stirring to achieve a target volume of 1500 mL.

The pharmaceutical aqueous solution formulation of the invention (above) is filled into 20 ml vials to a target volume of 7 ml. The vials are partially stoppered (not sealed) with a 20 mm Gray Lyo D777-1 V10-F597W FluroTec Siliconised (trade mark) stopper. The vials are loaded into stainless steel trays and inserted into a LSL1000 (trade mark) freeze dryer. The freeze drying cycle is then run in accordance with conventional procedures.

On completion of the freeze drying cycle the freeze dryer is back-filled with sterile filtered nitrogen to a set point of 500 Torr (ca. 666 mbar or 66,600 Pascals), and the vials are fully closed using the stoppers. The freeze dryer is then vented to atmospheric pressure using sterile filtered air and the vials are unloaded from the freeze dryer.

Each vial contains the freeze dried (lyophilised) formulation as a solid.

Further Examples of the Preparation of Pharmaceutical Aqueous Solution Formulations Comprising 1-(4-{[4-(dimethylamino)piperidin-1-yl] carbonyl}phenyl)-3-[4-(4,6-dimorpholin-4-yl-1,3,5-triazin-2-yl)phenyl]urea, a Beta- or Gamma-Cyclodextrin and a Pharmaceutically Acceptable Organic or Inorganic Acid The following, tabulated Examples (indicated by a tick or a cross) (target volume=100 ml) were prepared using similar methods to those of Examples 1-3 using the ingredient specification tabulated below.

These Examples were analysed by the visual method defined in European Pharmacopoeia Method 2.9.20 and the OPM method both as described in Example 1. The results are also tabulated below.

In this Table "particle-free" means that the the formulation was visually clear and free of visible crystallites or particulates and meet the required "clear solution" definition as described earlier.

| | | | API mg/ml/API mM | | | | | | | | | | | |
|---|---|---|---|---|---|---|---|---|---|---|---|---|---|---|
| | | | 10/ 16.7 | 15/ 24.4 | 20/ 32.5 | 25/ 40.6 | 30/ 48.7 | 35/ 56.8 | 40/ 65.0 | 45/ 73.1 | 50/ 81.2 | 55/ 89.3 | 60/ 97.5 | 65/ 105.6 | 70/ 113.7 |
| HCL | 100 mM | SBECD (20% w/v) | ✓ | ✓ | ✓ | ✓ (1) | ✓ (1) | x (2) | | | | | | | |

-continued

| | | | API mg/ml/API mM | | | | | | | | | | | | |
|---|---|---|---|---|---|---|---|---|---|---|---|---|---|---|---|
| | | | 10/16.7 | 15/24.4 | 20/32.5 | 25/40.6 | 30/48.7 | 35/56.8 | 40/65.0 | 45/73.1 | 50/81.2 | 55/89.3 | 60/97.5 | 65/105.6 | 70/113.7 |
| HCL | 100 mM | HPBCD (20% w/v) | | | | ✓ | ✓ (1) | ✓ (1) | x (2) | x (2) | | | | | |
| HCL | 100 mM | Gamma-CD (20% w/v) | | | | ✓ | ✓ (1) | ✓ (1) | ✓ (1) | ✓ (1) | ✓ (1) | ✓ (1) | ✓ (1) | x (2) | |
| Ortho-phosphoric acid | 100 mM | SBECD (20% w/v) | ✓ | ✓ | ✓ | ✓ (1) | ✓ (1) | ✓ (1) | x (2) | | | | | | |
| Ortho-phosphoric acid | 100 mM | HPBCD (20% w/v) | | | | ✓ | ✓ (1) | ✓ (1) | x (2) | x (2) | | | | | |
| Ortho-phosphoric acid | 100 mM | Gamma-CD (20% w/v) | | | | ✓ (1) | ✓ (1) | ✓ (1) | ✓ (1) | ✓ (1) | ✓ (1) | x (2) | | | |
| Lactic acid* | 100 mM | HPBCD (20% w/v) | ✓ | ✓ | ✓ | ✓ | ✓ (1) | x (2) | | | | | | | |
| Lactic acid* | 100 mM | Alpha CD (20% w/v) | x (2) | x (2) | x (2) | x (2) | x (2) | x (2) | | | | | | | |
| Lactic acid* | 100 mM | Gamma-CD (20% w/v) | ✓ | ✓ | ✓ | ✓ (1) | ✓ (1) | x (2) | | | | | | | |
| Lactic acid* | 100 mM | SBECD (20% w/v) | ✓ | ✓ | ✓ (1) | ✓ (1) | x (2) | | | | | | | | |
| Tartaric acid* | 100 mM | SBECD (20% w/v) | ✓ | ✓ | ✓ (1) | ✓ (1) | x (2) | | | | | | | | |
| Tartaric acid* | 100 mM | HPBCD (20% w/v) | | | | ✓ | ✓ (1) | ✓ (1) | x (2) | x (2) | | | | | |
| Tartaric acid* | 100 mM | Gamma-CD (20% w/v) | | | ✓ | ✓ | ✓ (1) | ✓ (1) | ✓ (1) | ✓ (1) | ✓ (1) | ✓ (1) | ✓ (1) | ✓ (1) | x (2) |
| Malic acid* | 100 mM | SBECD (20% w/v) | ✓ | ✓ | ✓ (1) | ✓ (1) | x (2) | | | | | | | | |
| Malic acid* | 100 mM | HPBCD (20% w/v) | | | | ✓ | ✓ (1) | ✓ (1) | x (2) | x (2) | | | | | |
| Malic acid* | 100 mM | Gamma-CD (20% w/v) | | | ✓ | ✓ (1) | ✓ (1) | ✓ (1) | ✓ (1) | ✓ (1) | ✓ (1) | ✓ (1) | ✓ (1) | ✓ (1) | x (2) |
| Citric acid | 100 mM | SBECD (20% w/v) | ✓ | ✓ (1) | ✓ (1) | x (2) | | | | | | | | | |
| Citric acid | 100 mM | HPBCD (20% w/v) | | ✓ | ✓ (1) | ✓ (1) | x (2) | x (2) | | | | | | | |
| Citric acid | 100 mM | Gamma-CD (20% w/v) | | | ✓ | ✓ (1) | ✓ (1) | ✓ (1) | ✓ (1) | ✓ (1) | ✓ (1) | ✓ (1) | x (2) | | |
| Succinic acid | 100 mM | SBECD (20% w/v) | ✓ | ✓ (1) | ✓ (1) | x (2) | | | | | | | | | |
| Succinic acid | 100 mM | HPBCD (20% w/v) | | ✓ | ✓ (1) | ✓ (1) | x (2) | x (2) | | | | | | | |
| Succinic acid | 100 mM | Gamma-CD (20% w/v) | | | ✓ | ✓ (1) | ✓ (1) | ✓ (1) | ✓ (1) | ✓ (1) | ✓ (1) | ✓ (1) | ✓ (1) | ✓ (1) | x (2) |
| P-toluene-sulfonic | 100 mM | HPBCD (20% w/v) | x (2) | x (2) | x (2) | x (2) | x (2) | x (2) | x (2) | x (2) | x (2) | x (2) | x (2) | | |
| P-toluene-sulfonic | 100 mM | SBECD (20% w/v) | x (2) | x (2) | x (2) | x (2) | x (2) | x (2) | x (2) | x (2) | x (2) | x (2) | x (2) | | |
| Acetic acid | 100 mM | HPBCD (20% w/v) | | ✓ (1) | x (2) | | | | | | | | | | |
| Acetic acid | 100 mM | SBECD (20% w/v) | | ✓ (1) | x (2) | | | | | | | | | | |
| Acetic acid | 100 mM | Gamma-CD (20% w/v) | | ✓ (1) | x (2) | | | | | | | | | | |
| Maleic acid | 100 mM | HPBCD (20% w/v) | | | ✓ (1) | x (2) | x (2) | | | | | | | | |
| Maleic acid | 100 mM | SBECD (20% w/v) | | | | ✓ (1) | ✓ (1) | x (2) | | | | | | | |
| Maleic acid | 100 mM | Gamma-CD (20% w/v) | | ✓ (1) | x (2) | | | | | | | | | | |

Key
API = 1-(4-{[4-(dimethylamino)piperidin-1-yl]carbonyl}phenyl)-3-[4-(4,6-dimorpholin-4-yl-1,3,5-triazin-2-yl)phenyl]urea
* = acid used in racemic form
HPBCD = 2-hydroxypropyl-beta-cyclodextrin
SBECD = sulphobutylether-β-cyclodextrin
GammaCD = gamma-cyclodextrin
AlphaCD = alpha-cyclodextrin
(1) = particle-free (and non-opalescent). All these Examples studied are free of visible crystallite or particulate matter and meet the required "clear solution" definition as described earlier.
(2) = particulate suspension Chemical Stability of a Lyophilised Solid Formulation of the Invention A sample of a lyophilised formulation of the invention was prepared in accordance with Example 6 ("Sample A").

Separate portions of Sample A were each housed in 20 mL clear vials and one was stored at 25° C./60% Relative Humidity ("RH") for 6 months, and the other was stored at 40° C./75% RH for 6 months.

After 6 months storage as above, the separate Samples were each tested for chemical purity using Ultra High Performance Liquid Chromatography (UHPLC) using the following methodology in order to measure any chemical degradation during the period of testing.

UHPLC Method

The solutions, samples, standards and UHPLC method are as below:

Reference Standard: 1-(4-{[4-(dimethylamino)piperidin-1-yl]carbonyl}phenyl)-3-[4-(4,6-dimorpholin-4-yl-1,3,5-triazin-2-yl)phenyl]urea with a known potency value.

Diluent: Acetonitrile/Water/Trifluoroacetic acid (750:250:1 v/v/v)

Mobile Phase A: Acetonitrile/Water/Trifluoroacetic acid (97:3:1 v/v/v)

Mobile Phase B: Acetonitrile/Trifluoroacetic acid (1000:1 v/v).

(Note: larger or smaller volumes of solutions may be prepared using the appropriate ratio of components)

Standard and Check Standard Preparations:

Accurately prepare two solutions of ca. 0.2 mg/ml (+/− 10%) of 1-(4-{[4-(dimethylamino) piperidin-1-yl]carbonyl}phenyl)-3-[4-(4,6-dimorpholin-4-yl-1,3,5-triazin-2-yl)phenyl]urea Reference Standard in Diluent, and record the concentrations accurately of both. These are the Standard and Check standard preparations.

Sensitivity Solution:

Accurately dilute the Standard preparation to a concentration of approximately 0.1 microgram/ml of 1-(4-{[4-(dimethylamino)piperidin-1-yl]carbonyl}phenyl)-3-[4-(4,6-dimorpholin-4-yl-1,3,5-triazin-2-yl)phenyl]urea using the Diluent.

Sample Preparation:

Reconstitute Sample A after storage by adding 7.0 ml of water to each in the 20 ml vial, shake the vial to dissolve the solid and wait for the bubbles to disappear. Transfer 1.0 ml of the solution into a 50 ml volumetric flask. Dilute to the set volume with Diluent.

Chromatographic Conditions:

Liquid chromatographic system—Agilent 1290 Infinity II™ with 380 µl Jet Weaver™

Column: Waters BEH C18™ 15 cm×2.1 mm, 1.7 µm or equivalent

Column Temperature: 20° C.

Injection Volume: 2 µL

Flow Rate: 0.25 mL/min.

Flow Cell: G4212-60008, 10 mm path length, 1.0 µL

Detection: UV at 240 nm/4 nm slit width

Run Time: 77 minutes

Mobile Phase A

Mobile Phase B

Needle wash solution: Water/Acetonitrile (95:5 v/v), multi wash 20 s.

Seal wash solution: Water/Propan-2-ol (90:10 v/v)

| Linear Gradient Table: | | |
|---|---|---|
| Time (minutes) | % Mobile Phase A | % Mobile Phase B |
| 0 | 95 | 5 |
| 5.0 | 95 | 5 |
| 31.4 | 78 | 22 |
| 42.3 | 78 | 22 |
| 65.0 | 5 | 95 |
| 67.0 | 5 | 95 |
| 67.1 | 95 | 5 |
| 77.0 | 95 | 5 |

Explanatory Notes

Condition the UHPLC system, prior to starting the analysis, with the mobile phases.

Prior to running samples, ensure that the system is suitable for use by injecting blank diluent, sensitivity solution and standard preparation using the chromatographic conditions above.

The following criteria must be satisfied on initial UHPLC set-up or after any significant change to the system. It is recommended to inject at least one conditioning blank prior to testing system suitability.

| Test | No. of Injections | Solution | Criteria |
|---|---|---|---|
| Blank | 1 | Diluent | Free from interfering peaks |
| Signal to Noise | 1 | Sensitivity Solution | European Pharmacopoeia (EP)/United States Pharmacopoeia (USP) Signal to Noise ≥ 10 |
| Repeatability | 5 | Standard preparation | Relative Standard Deviation ≤ 2.0% |
| Retention time | 1* | | 38-44 minutes |
| Efficiency (Plate)** | | | Plate number for 1-(4-{[4-(dimethylamino)piperidin-1-yl]carbonyl}phenyl)-3-[4-(4,6-dimorpholin-4-yl-1,3,5-triazin-2-yl)phenyl]urea peak ≥ 10,000 |
| Peak Asymmetry (T)** | | | 0.9 ≤ T ≤ 2.0 for 1-(4-{[4-(dimethylamino)piperidin-1-yl]carbonyl}phenyl)-3-[4-(4,6-dimorpholin-4-yl-1,3,5-triazin-2-yl)phenyl]urea peak |
| Resolution | 1 | | Resolution between 1-(4-{[4-(dimethylamino)piperidin-1-yl]carbonyl}phenyl)-3-[4-(4,6-dimorpholin-4-yl-1,3,5-triazin-2-yl)phenyl]urea peak and Degradant 2 [((4-(4,6-dimorpholino-1,3,5-triazin-2-yl)phenyl)-I2-azaneyl)((4-(4-(methyl-I2-azaneyl)piperidine-1-carbonyl)phenyl)-I2-azaneyl)methanone ≥ 1.0] |

*Use average of all system suitability (repeatability) injections.
**Refer to United States Pharmacopoeia (USP) calculation equations for Efficiency and Peak Asymmetry.

Inject the check standard preparation according to the chromatographic conditions above. The response factor (calculated from the area, standard weight, dilution factor and purity factor of the standard) of this check standard preparation must be within ±2% of the standard preparation.

After the system suitability has been demonstrated, inject the blank solution, standard preparation and prepared test samples, followed by an injection of the standard preparation, according to the chromatographic conditions above. It is recommended that no more than 6 test samples be injected between standard preparation injections. For each injection (standard and sample), measure the retention time and area of the 1-(4-{[4-(dimethylamino) piperidin-1-yl]carbonyl}phenyl)-3-[4-(4,6-dimorpholin-4-yl-1,3,5-triazin-2-yl)phenyl]urea peak in each chromatogram. For each sample injection, also measure the retention times and peak area of any peaks present in the sample injection that do not appear in the blank injection. Do not integrate gradient artifacts, if present. Compare the blank injection chromatogram to the sample chromatogram to determine which peaks in the sample are related to the blank and gradient artifact peaks. Calculate the % w/w degradants and report the individual degradant peaks which are at or above 0.05% w/w. Unknown degradants should be reported individually by their relative retention time. Known degradants should be reported individually by name.

The results are summarised in the Table below.

Key

NMT=Not More Than.

RRT=Relative Retention Time

Degradant 1

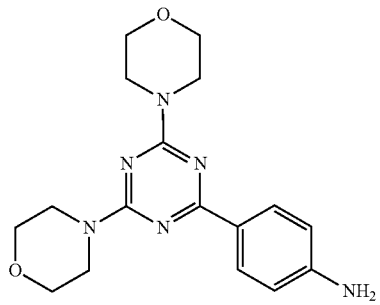 [SMILES: Nc1ccc(-c2nc(N3CCOCC3)nc(N3CCOCC3)n2)cc1]

Degradants 2, 3 and 4

These were each characterised by their RRT only.

| Degradant | Sample A results | | | |
|---|---|---|---|---|
| | Acceptance Criteria | Initial | 25° C./ 60% RH 6 months | 40° C./ 75% RH 6 months |
| Degradant 1 (RRT~0.72) | NMT 0.5% | 0.10% | 0.12% | 0.14% |
| Degradant 2 (RRT~0.98) | NMT 1.1% | NMT0.05% | NMT 0.05% | 0.10% |
| Degradant 3 (RRT~1.07) | NMT 0.5% | NMT0.05% | NMT 0.05% | 0.13% |
| Degradant 4 (RRT~1.17) | NMT 0.5% | 0.06% | NMT 0.05% | NMT0.05% |
| Total Degradants | NMT 3.0% | 0.16% | 0.12% | 0.37% |

CONCLUSION

The results show that Sample A is chemically stable for at least 6 months at 25° C./60% RH and for at least 6 months at 40° C./75% RH.

The invention claimed is:

1. A pharmaceutical aqueous formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, or a pharmaceutically acceptable organic or inorganic acid salt thereof, a pharmaceutically acceptable organic or inorganic acid, a pharmaceutically acceptable beta- or gamma-cyclodextrin and water, wherein 1-(4-{[4-(dimethylamino) piperidin-1-yl]carbonyl}phenyl)-3-[4-(4,6-dimorpholin-4-yl-1,3,5-triazin-2-yl)phenyl]urea is present at a solution concentration of at least 6 mg/ml and wherein sufficient of the pharmaceutically acceptable organic or inorganic acid and pharmaceutically acceptable beta- or gamma-cyclodextrin are present to provide a clear solution, with the proviso that the organic or inorganic acid (including a salt thereof) is not a sulphonic acid.

2. A pharmaceutical aqueous formulation as claimed in claim 1 wherein the pharmaceutically acceptable organic or inorganic acid is selected from lactic acid, acetic acid, maleic acid, succinic acid, citric acid, malic acid, tartaric acid, hydrochloric acid or orthophosphoric acid.

3. A pharmaceutical aqueous formulation as claimed in claim 1 comprising 1-(4-{[4-(dimethylamino)piperidin-1-yl]carbonyl}phenyl)-3-[4-(4,6-dimorpholin-4-yl-1,3,5-triazin-2-yl)phenyl]urea, or a lactate salt thereof, lactic acid, a pharmaceutically acceptable beta- or gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 6 to 30 mg/ml and wherein sufficient lactic acid and pharmaceutically acceptable beta- or gamma-cyclodextrin are present to provide a clear solution.

4. A pharmaceutical aqueous formulation as claimed in claim 3 comprising 1-(4-{[4-(dimethylamino)piperidin-1-yl]carbonyl}phenyl)-3-[4-(4,6-dimorpholin-4-yl-1,3,5-triazin-2-yl)phenyl]urea, lactic acid, a pharmaceutically acceptable beta- or gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 6 to 30 mg/ml and wherein sufficient lactic acid and pharmaceutically acceptable beta- or gamma-cyclodextrin are present to provide a clear solution.

5. A pharmaceutical aqueous formulation as claimed in claim 3 comprising a lactate salt of 1-(4-{[4-(dimethylamino)piperidin-1-yl]carbonyl}phenyl)-3-[4-(4,6-dimorpholin-4-yl-1,3,5-triazin-2-yl)phenyl]urea, lactic acid, a pharmaceutically acceptable beta- or gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 6 to 30 mg/ml and wherein sufficient lactic acid and pharmaceutically acceptable beta- or gamma-cyclodextrin are present to provide a clear solution.

6. A pharmaceutical aqueous formulation as claimed in claim 3 comprising 1-(4-{[4-(dimethylamino)piperidin-1-yl]carbonyl}phenyl)-3-[4-(4,6-dimorpholin-4-yl-1,3,5-triazin-2-yl)phenyl]urea, or a lactate salt thereof, lactic acid, a pharmaceutically acceptable beta- or gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 6 to 25 mg/ml and wherein sufficient lactic acid and pharmaceutically acceptable beta- or gamma-cyclodextrin are present to provide a clear solution.

7. A pharmaceutical aqueous formulation as claimed in claim 3 comprising 1-(4-{[4-(dimethylamino)piperidin-1-yl]carbonyl}phenyl)-3-[4-(4,6-dimorpholin-4-yl-1,3,5-triazin-2-yl)phenyl]urea, lactic acid, a pharmaceutically acceptable beta- or gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 6 to 25 mg/ml and wherein sufficient lactic acid and pharmaceutically acceptable beta- or gamma-cyclodextrin are present to provide a clear solution.

8. A pharmaceutical aqueous formulation as claimed in claim 3 comprising a lactate salt of 1-(4-{[4-(dimethylamino)piperidin-1-yl]carbonyl}phenyl)-3-[4-(4,6-dimorpholin-4-yl-1,3,5-triazin-2-yl)phenyl]urea, lactic acid, a pharmaceutically acceptable beta- or gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 6 to 25 mg/ml and wherein sufficient lactic acid and pharmaceutically acceptable beta- or gamma-cyclodextrin are present to provide a clear solution.

9. A pharmaceutical aqueous formulation as claimed in claim 3 wherein the pharmaceutically acceptable beta- or gamma-cyclodextrin used is 2-hydroxypropyl-beta-cyclodextrin, sulphobutylether-β-cyclodextrin (SBECD) or gamma-cyclodextrin.

10. A pharmaceutical aqueous formulation as claimed in claim 9 wherein the pharmaceutically acceptable beta- or gamma-cyclodextrin used is 2-hydroxypropyl-beta-cyclodextrin or gamma-cyclodextrin.

11. A pharmaceutical aqueous formulation as claimed in claim 3 comprising 1-(4-{[4-(dimethylamino)piperidin-1-yl]carbonyl}phenyl)-3-[4-(4,6-dimorpholin-4-yl-1,3,5-triazin-2-yl)phenyl]urea, or a lactate salt thereof, lactic acid, sulphobutylether-β-cyclodextrin (SBECD) and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 6 to 25 mg/ml and wherein sufficient lactic acid and sulphobutylether-β-cyclodextrin (SBECD) are present to provide a clear solution.

12. A pharmaceutical aqueous formulation as claimed in claim 3 comprising 1-(4-{[4-(dimethylamino)piperidin-1-yl]carbonyl}phenyl)-3-[4-(4,6-dimorpholin-4-yl-1,3,5-triazin-2-yl)phenyl]urea, or a lactate salt thereof, lactic acid, 2-hydroxypropyl-beta-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 6 to 30 mg/ml and wherein sufficient lactic acid and 2-hydroxypropyl-beta-cyclodextrin are present to provide a clear solution.

13. A pharmaceutical aqueous formulation as claimed in claim 3 comprising 1-(4-{[4-(dimethylamino)piperidin-1-yl]carbonyl}phenyl)-3-[4-(4,6-dimorpholin-4-yl-1,3,5-triazin-2-yl)phenyl]urea, or a lactate salt thereof, lactic acid, 2-hydroxypropyl-beta-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 6 to 30 mg/ml and wherein the lactic acid concentration is from 10 to 100 mM and the 2-hydroxypropyl-beta-cyclodextrin concentration is from 15 to 120 mg/ml to provide a clear solution.

14. A pharmaceutical aqueous formulation as claimed in claim 3 comprising 1-(4-{[4-(dimethylamino)piperidin-1-yl]carbonyl}phenyl)-3-[4-(4,6-dimorpholin-4-yl-1,3,5-triazin-2-yl)phenyl]urea, lactic acid, 2-hydroxypropyl-beta-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 10 to 30 mg/ml and wherein the lactic acid concentration is from 20 to 100 mM and the 2-hydroxypropyl-beta-cyclodextrin concentration is from 35 to 120 mg/ml to provide a clear solution.

15. A pharmaceutical aqueous formulation as claimed in claim 1 wherein from 2 to 30% w/v of the cyclodextrin is used.

16. A lyophilized formulation obtainable by freeze drying the pharmaceutical aqueous formulation as claimed in claim 1.

17. A pharmaceutical aqueous formulation obtainable as a clear solution by reconstitution or constitution of a lyophilized formulation as claimed in claim 16 using water or an aqueous solution comprising a tonicity modifier.

18. A pharmaceutical aqueous formulation as claimed in claim 17 wherein the tonicity modifier is dextrose, sucrose or mannitol, or is a mixture of any 2 or more thereof.

19. A pharmaceutical aqueous formulation as claimed in claim 1 that is adjusted, as necessary, to have a pH suitable for intravenous or parenteral administration.

20. A method of treatment of cancer in a mammal comprising treatment of the mammal with an effective amount of the pharmaceutical aqueous formulation as claimed in claim 1.

21. A pharmaceutical aqueous formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, or a acetate salt thereof, acetic acid, a pharmaceutically acceptable beta- or gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 3 to 15 mg/ml and wherein sufficient acetic acid and pharmaceutically acceptable beta- or gamma-cyclodextrin are present to provide a clear solution.

22. A pharmaceutical aqueous formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, or a maleate salt thereof, maleic acid, a pharmaceutically acceptable beta- or gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 3 to 30 mg/ml and wherein sufficient maleic acid and pharmaceutically acceptable beta- or gamma-cyclodextrin are present to provide a clear solution.

23. A pharmaceutical aqueous formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, or a succinate salt thereof, succinic acid, a pharmaceutically acceptable beta- or gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 3 to 65 mg/ml and wherein sufficient succinic acid and pharmaceutically acceptable beta- or gamma-cyclodextrin are present to provide a clear solution.

24. A pharmaceutical aqueous formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, or a citrate salt thereof, citric acid, a pharmaceutically acceptable beta- or gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 3 to 55 mg/ml and wherein sufficient citric acid and pharmaceutically acceptable beta- or gamma-cyclodextrin are present to provide a clear solution.

25. A pharmaceutical aqueous formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, or a malate salt thereof, malic acid, a pharmaceutically acceptable beta- or gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 3 to 65 mg/ml and wherein sufficient malic acid and pharmaceutically acceptable beta- or gamma-cyclodextrin are present to provide a clear solution.

26. A pharmaceutical aqueous formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, or a tartrate salt thereof, tartaric acid, a pharmaceutically acceptable beta- or gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 3 to 65 mg/ml and wherein sufficient tartaric acid and pharmaceutically acceptable beta- or gamma-cyclodextrin are present to provide a clear solution.

27. A pharmaceutical aqueous formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, or a hydrochloride salt thereof, hydrochloric acid, a pharmaceutically acceptable beta- or gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 3 to 60 mg/ml and wherein sufficient hydrochloric acid and pharmaceutically acceptable beta- or gamma-cyclodextrin are present to provide a clear solution.

28. A pharmaceutical aqueous formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, or a phosphate salt thereof, orthophosphoric acid, a pharmaceutically acceptable beta- or gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 4 to 50 mg/ml and wherein sufficient orthophosphoric acid and pharmaceutically acceptable beta- or gamma-cyclodextrin are present to provide a clear solution.

* * * * *